US00PP37105P2

(12) United States Plant Patent
Schoemaker

(10) Patent No.: US PP37,105 P2
(45) Date of Patent: Nov. 25, 2025

(54) ***HYDRANGEA* PLANT NAMED 'LC NO25'**

(50) Latin Name: *Hydrangea paniculata*
Varietal Denomination: LC NO25

(71) Applicant: Alex F. Schoemaker, Boskoop (NL)

(72) Inventor: Alex F. Schoemaker, Boskoop (NL)

(73) Assignee: Alex Schoemaker Living Creations Holding B.V. (NL)

( * ) Notice: Subject to any disclaimer, the term of this patent is extended or adjusted under 35 U.S.C. 154(b) by 0 days.

(21) Appl. No.: 19/056,305

(22) Filed: Feb. 18, 2025

(51) Int. Cl.
*A01H 5/00* (2018.01)
*A01H 6/48* (2018.01)

(52) U.S. Cl.
USPC ..... Plt./250
CPC ..... *A01H 6/48* (2018.05); *A01H 5/00* (2013.01)

(58) Field of Classification Search
USPC ..... Plt./250
See application file for complete search history.

*Primary Examiner* — Susan Mccormick Ewoldt

(57) ABSTRACT

A new and distinct cultivar of *Hydrangea paniculata* plant named 'LC NO22' is disclosed, characterized by sturdy stems on medium sized, compact plants. Plants are highly floriferous with globular panicles fully covering the plant. The sterile flowers have ornamental sepals that begin green-white, turn light pink and mature to dark pink. Foliage is distinctively healthy and strong. The new variety is a *Hydrangea*, typically produced as an outdoor ornamental plant.

3 Drawing Sheets

Latin name of the genus and species: *Hydrangea paniculata.*

Cultivar denomination: 'LC NO25'.

BACKGROUND OF THE INVENTION

The new cultivar is a product of a planned breeding program conducted by the inventor at a commercial greenhouse in Boskoop, the Netherlands. The inventor crossed the seed parent, the unpatented proprietary seedling referred to as '1408-1' with the pollen parent, the unpatented proprietary seedling referred to as '1318-1' in July of 2018. The new cultivar 'LC NO25' was selected by the inventor in August of 2020 from seedlings developed from the 2018 crossing.

Asexual reproduction of the new cultivar 'LC NO25' was first performed during September of 2020 at the same commercial greenhouse in Boskoop, the Netherlands, by softwood cuttings. Through subsequent propagation, multiple additional generations have been reproduced, having shown that the unique features of this cultivar are stable and reproduced true to type.

The inventor has filed an application with the CPVO Feb. 17, 2025. This disclosure falls within the exception allowed under 102(b)(1).

SUMMARY OF THE INVENTION

The cultivar 'LC NO25' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'LC NO25'. These characteristics in combination distinguish 'LC NO25' as a new and distinct *Hydrangea* cultivar:

1. Sturdy stems.
2. Medium-sized, compact plant.
3. Highly floriferous plants with panicles fully covering the plant.
4. Interesting color changing sepals, beginning green-white, turning light pink and maturing to dark pink.
5. Healthy, strong foliage.
6. Very well-branched plants.
7. Globular panicles.

PARENT COMPARISON

Plants of 'LC NO25' are similar to plants of the seed parent in most horticultural characteristics, however, plants of 'LC NO25' differ from plants of the seed parent in the following:

1. Plants of the new cultivar are more compact than plants of the seed parent which has a more open habit.
2. Panicles of the new cultivar are more globular; panicles of the seed parent are conical.

Plants of 'LC NO25' are similar to plants of both parents in most horticultural characteristics, however, plants of 'LC NO25' differ in the following:

1. Plants of the new cultivar are shorter than plants of the pollen parent.
2. Foliage of the new cultivar is less glossy than foliage of the pollen parent.
3. The new cultivar has denser panicles than the pollen parent.
4. Sepal color of the new cultivar begins green-white, turns light pink and matures to dark pink; sepal color of the pollen parent is dark purple-red.

COMMERCIAL COMPARISONS

Plants of 'LC NO25' can be compared to plants of the commercial cultivar *Hydrangea* 'Rensun', U.S. Plant Pat.

No. 25,438. Plants of 'LC NO25' are similar to plants of 'Rensun' in most horticultural characteristics, however, plants of 'LC NO25' differ in the following:

1. 'LC NO25' has a globular inflorescence; 'Rensun' has a more elongated, conical inflorescence.
2. 'LC NO25' has darker green foliage than 'Rensun'.
3. 'LC NO25' has darker pink sepals in both the maturing and mature phase.

Plants of the new cultivar *Hydrangea* 'LC NO25' can be compared to the commercial cultivar *Hydrangea* 'Silver Dollar', unpatented. Plants of 'LC NO25' are similar to plants of 'Silver Dollar' in most horticultural characteristics, however, plants of 'LC NO25' differ in the following:

1. Plants of the new cultivar are much more compact than plants of this comparator.
2. 'LC NO25' flowers earlier than this comparator.
3. 'LC NO25' has lighter green leaves than this comparator.
4. 'LC NO25' has more panicles per plant than this comparator.

Plants of the new cultivar *Hydrangea* 'LC NO25' can be compared to the commercial cultivar *Hydrangea* 'LC NO10', U.S. Plant Pat. No. 33,233. Plants of 'LC NO25' are similar to plants of 'LC NO10' in most horticultural characteristics, however, plants of 'LC NO25' differ in the following:

1. Branches of the new cultivar are stronger than branches of this comparator.
2. 'LC NO25' produces more branches than this comparator.
3. Foliage of 'LC NO25' does not droop and turn color in hot weather as seen in 'LC NO1'.

BRIEF DESCRIPTION OF THE PHOTOGRAPHS

The accompanying photograph in FIG. 1 illustrates in full color a typical plant of 'LC NO25' grown in 28 cm pot outdoors in Boskoop, the Netherlands. This plant is approximately 3 years old, photographed in July.

Figure 1:
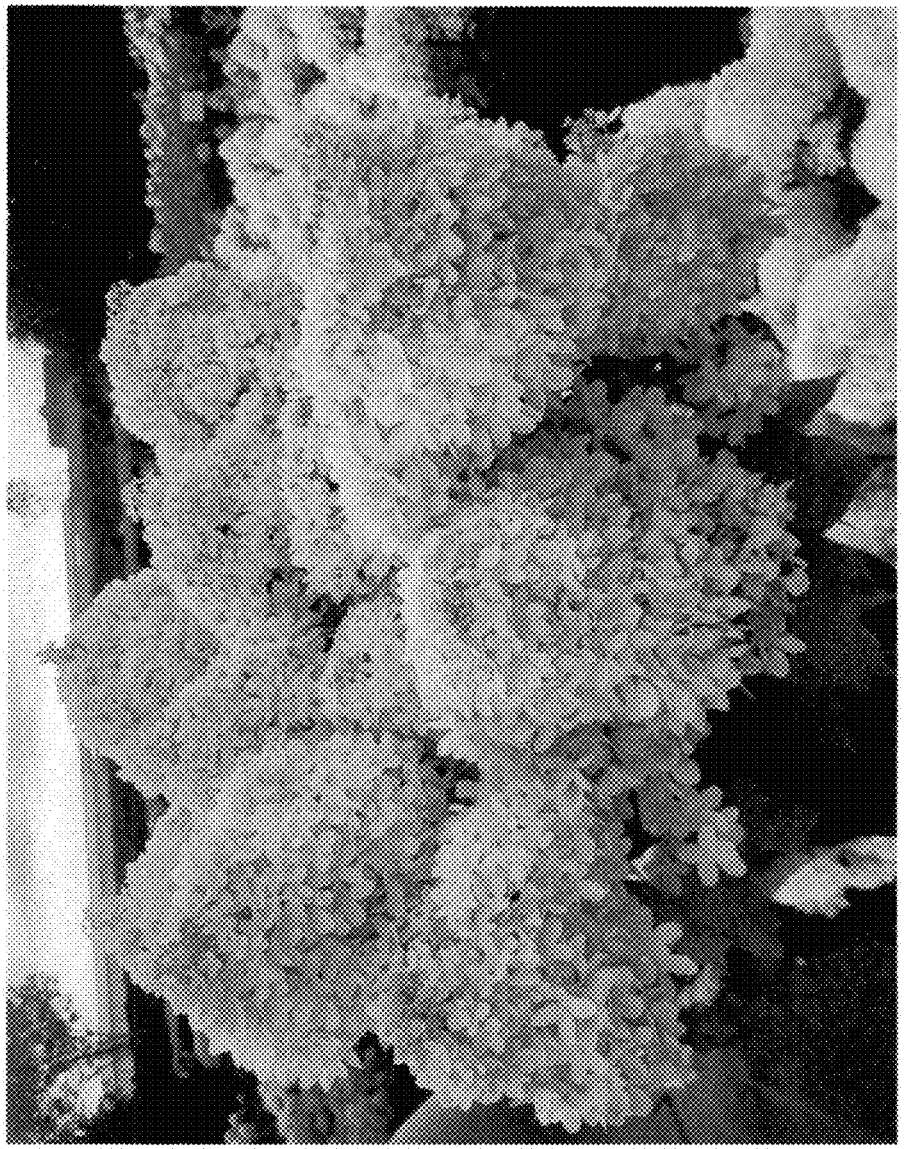
Figure 2:
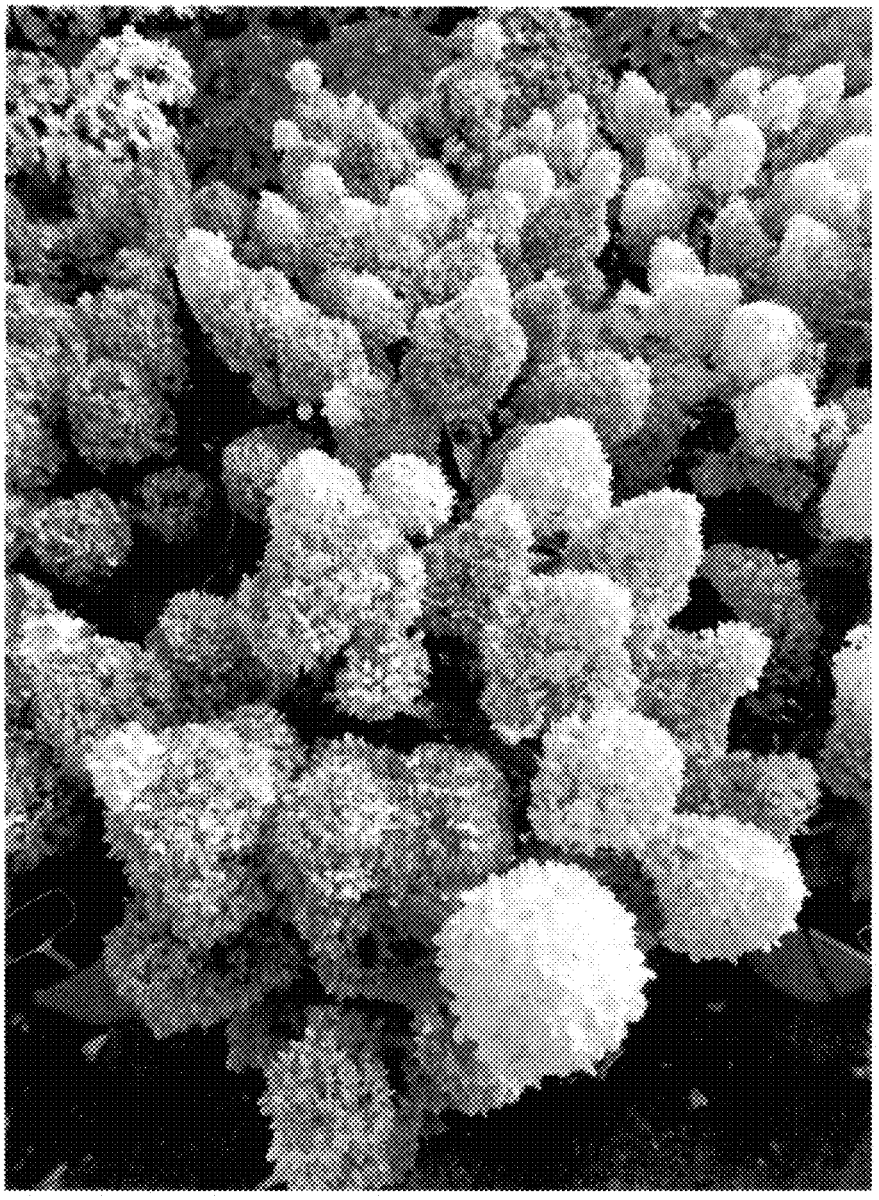
FIG. 2 illustrates in full color a typical plant of 'LC NO25' in a 28 cm pot during August, with developing pink coloration to the sepals.
Figure 3:
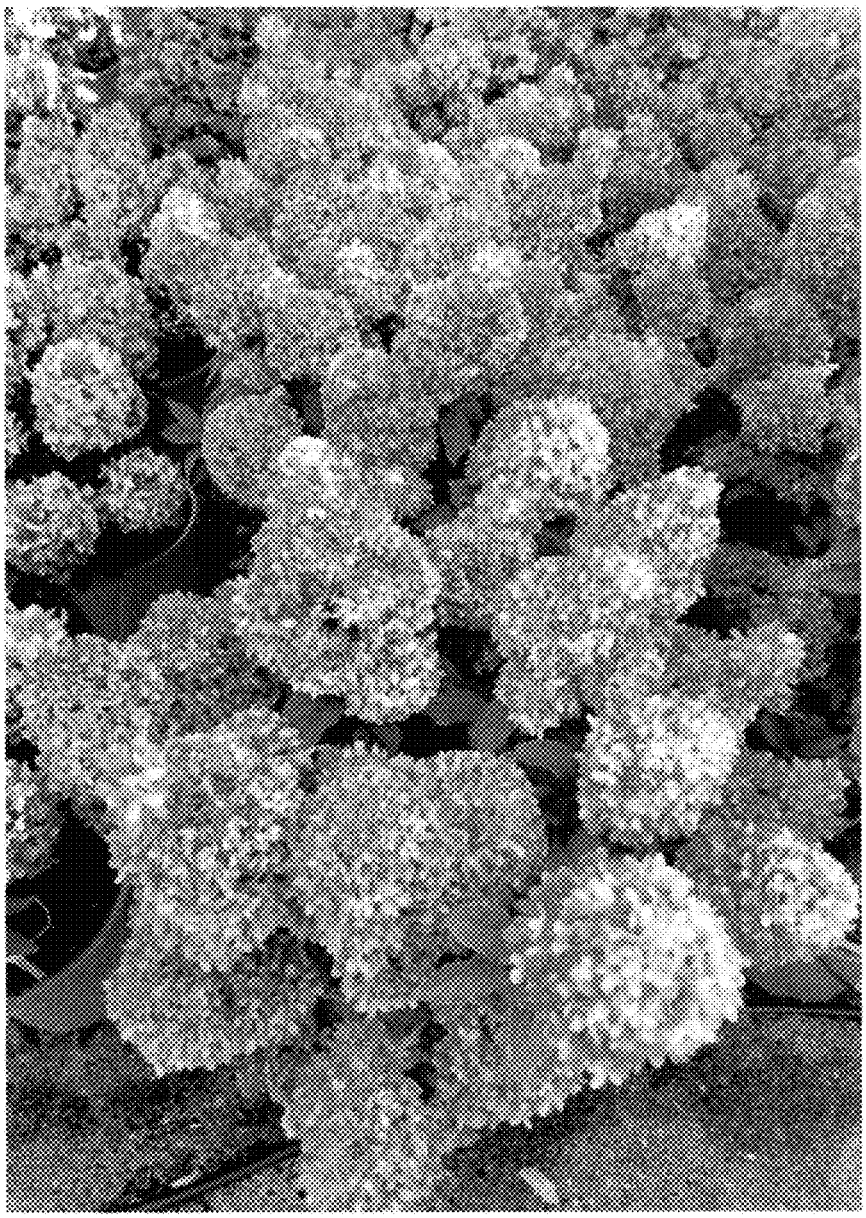
FIG. 3 illustrates in full color a typical plant of 'LC NO25' in a 28 cm pot during September, having the deeper coloration typical of the sepals a their fully mature stage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, except where general terms of ordinary dictionary significance are used. The following observations and measurements describe 'LC NO25' plants grown outdoors in Boskoop, the Netherlands. The plants were about 3-years old planted in a field. Temperatures ranged from about 5° C. to 10° C. at night to 18° C. to 27° C. during the day. No artificial light, photoperiodic treatments were given to the plants. Measurements and numerical values represent averages of typical plant types.

Botanical classification: *Hydrangea paniculata* 'LC NO25'.

PROPAGATION

Typical method: Softwood cuttings.

Roots: Thin, freely branching, fibrous, moderately dense. Tan and white in color, not accurately measured with R.H.S. chart.

PLANT

Growth habit: Compact and semi-upright. Deciduous flowering shrub.

Shape: Rounded.

Height: 60 cm. 90 cm at full maturity.

Plant spread: 67 cm. 90 cm at full maturity.

Stem:

*Branching*.—Very free branching.

*Number of branches*.—About 9 main stems and 25 lateral branches when planted with 3 cuttings in a pot.

*Shape*.—Round.

*Color*.—Immature: RHS Yellow-Green 145A. Mature: RHS Yellow-Green 144B with Greyed-Purple 187C. Woody stems Brown 200D with Greyed-Brown N199D.

*Length*.—Average 42 cm.

*Width*.—5 mm.

*Strength*.—Very strong.

*Texture*.—Glabrous.

*Aspect*.—Straight, occurring at 60 degrees from center.

*Internode Length*.—7 cm.

FOLIAGE

Leaf:

*Arrangement*.—Opposite.

*Shape*.—Ovate.

*Length*.—7 to 9.3 cm.

*Width*.—4 to 5.5 cm.

*Apex*.—Acute.

*Base*.—Rounded to obtuse.

*Margin*.—Moderately serrate.

*Texture of top surface*.—Pubescent.

*Texture of bottom surface*.—Pubescent.

*Color*.—Young Foliage, Upper Side: RHS Green 137B. Young Foliage, Under Side: RHS Green 137C. Mature Foliage, Upper Side: RHS Green N137B. Mature Foliage, Under Side: RHS Green 138B.

Venation:

*Type*.—Pinnate.

*Color*.—Immature, Upper Side: RHS Yellow-Green 145A. Immature, Under Side: RHS Yellow-Green 145B. Mature, Upper Side: RHS Yellow-Green 145A. Mature, Under Side: RHS Green 138B.

Petiole:

*Length*.—1.8 cm.

*Width*.—2 mm.

*Color*.—Upper Side: RHS Yellow-Green 145A flushed Greyed-Purple 187B. Under Side: RHS Yellow-Green 145A flushed Greyed-Purple 187B.

*Texture*.—Upper Side: Lightly pubescent. Under Side: Lightly pubescent.

INFLORESCENCE

Natural flowering season: Late June to September/early October in Boskoop the Netherlands.
Inflorescence type: Panicle.
Lastingness: About 8 weeks.
Conspicuousness of fertile flowers: Absent.
Panicle:
*Shape*.—Globular.
*Height*.—22 cm.
*Diameter*.—19 cm.
Fragrance: Light sweet scent.
Sterile flowers:
*Flowers per inflorescence*.—Average around 400.
*Aspect*.—Outward and upright facing.
*Shape*.—Rotate.
*Length*.—2.5 cm.
*Diameter*.—4 mm.
*Persistence*.—Persistent.
Bud:
*Length*.—3 mm.
*Diameter*.—2 mm.
*Shape*.—Ovoid.
*Color*.—Emerging White-Green 157A and 157B, with Yellow-Green 144C.
Petals: 4 petals, each 1 mm in width and length. Orbicular in shape, glabrous texture. Apex obtuse, base obtuse, margin entire, colored same as the sepals.
Sepals:
*Number*.—4 or 5.
*Arrangement*.—Rotate.
*Shape*.—Elliptic to ovate.
*Tip*.—Rounded.
*Base*.—Attenuate.
*Margin*.—Entire.
*Length*.—9 to 12 mm.
*Width*.—6 to 7 mm.
*Texture*.—Upper side: Glabrous. Under side: Glabrous.
*Color*.—When Opening, Upper Side: Emerging Yellow-Green 144B, then 144D with 157A. When Opening, Under Side: Emerging Yellow-Green 144B, then 157A with a small amount of 144D. Fully Opened Summer, Upper Side: Green-White 157A with Yellow-Green 144D heavily flushed and streaked Red-Purple 63A and 63B. Fully Opened Summer, Under Side: Green-White 157A with hint of Red- Purple 63B. Fully Opened late Summer, Upper Side: Yellow-Green 145B with overall flush of Red-Purple 60C. Fully Opened late Summer, Under Side: Yellow-Green 145C with overall flush of Red-Purple 60A, 60B and 60C.
Pedicel:
*Length*.—1.6 cm.
*Diameter*.—1 mm.
*Strength*.—Moderately strong.
*Texture*.—Slightly pubescent.
*Color*.—RHS Green-White 157C.
Fertile flowers:
*Flowers per inflorescence*.—About 150.
*Aspect*.—Upright.
*Shape*.—Whorl.
*Length*.—7 mm.
*Diameter*.—4 mm.
Bud:
*Length*.—3 mm.
*Diameter*.—2 mm.
*Bud shape*.—Ovoid.
*Bud color*.—RHS White N155B tinged Red-Purple 63B.
Sepals:
*Number per flower*.—5.
*Arrangement*.—Rotate.
*Shape*.—Deltoid.
*Tip*.—Acuminate.
*Base*.—Broad cuneate.
*Margin*.—Entire.
*Length*.—1.5 mm.
*Width*.—1 mm.
*Texture*.—Upper Side: Glabrous. Under Side: Glabrous.
*Color*.—Upper Side: RHS Yellow-Green 145C. Under Side: RHS Yellow-Green 145C.
Petals:
*Number per flower*.—5.
*Arrangement*.—Rotate.
*Shape*.—Ovate.
*Tip*.—Acute.
*Base*.—Truncate.
*Margin*.—Entire.
*Length*.—3 mm.
*Width*.—1.5 mm.
*Texture*.—Upper Side: Glabrous. Under Side: Glabrous.
*Color*.—Upper Side: RHS White N155B mixed with 155C. Under Side: RHS White N155B mixed with 155C.
Pedicel:
*Length*.—1-2 mm.
*Diameter*.—1 mm.
*Strength*.—Moderate.
*Texture*.—Slightly pubescent.
*Color*.—RHS Green-White 157D.

REPRODUCTIVE ORGANS

Sterile flower:
Gynoecium: Not observed.
Stamens:
*Number*.—Most commonly 8.
*Filament length*.—2 mm.
*Filament color*.—RHS White NN155D.
Anthers:
*Shape*.—Linear.
*Length*.—0.5 mm.
*Color*.—RHS Greyed-Orange 163D.
*Pollen amount*.—Scant.
*Pollen color*.—RHS Greyed-Orange 163D.
Fertile flower:
Stamens:
*Number*.—Average 10.
*Filament length*.—3 mm.
*Filament color*.—RHS White NN155C.
Anthers:
*Shape*.—Broad oblong.
*Length*.—0.75 mm.
*Color*.—RHS Greyed-Yellow 160D.

*Pollen amount*.—Scant

*Pollen color*.—RHS Greyed-Yellow 160D.

Pistil:

*Number*.—Average 3.

*Length*.—2 mm.

Stigma:

*Shape*.—Club-shaped.

*Color*.—RHS Yellow-Green 145C.

*Style length*.—0.05 mm.

*Style color*.—RHS Yellow-Green 145B.

*Ovary color*.—RHS Yellow-Green 145A.

SEEDS

Not observed.

OTHER CHARACTERISTICS

Disease resistance: Neither resistance nor susceptibility to the normal diseases and pests of *Hydrangea* has been observed.

Cold tolerance: Hardy to −25° C.

What is claimed is:

1. A new and distinct cultivar of *Hydrangea* plant named 'LC NO25' as herein illustrated and described.

* * * * *